United States Patent [19]

Kaldany

[11] Patent Number: 5,501,664
[45] Date of Patent: *Mar. 26, 1996

[54] SUBCUTANEOUS DRUG DELIVERY DEVICE

[75] Inventor: Antoine Kaldany, Chestnut Hill, Mass.

[73] Assignee: InterMED, Inc., Chestnut Hill, Mass.

[ * ] Notice: The term of this patent shall not extend beyond the expiration date of Pat. No. 5,1217,419.

[21] Appl. No.: 271,027

[22] Filed: Jul. 6, 1994

Related U.S. Application Data

[63] Continuation of Ser. No. 965,638, Oct. 23, 1992, Pat. No. 5,358,474, which is a continuation-in-part of Ser. No. 908, 353, Jul. 6, 1992, abandoned, which is a continuation-in-part of Ser. No. 724,706, Jul. 2, 1991, Pat. No. 5,127,419.

[51] Int. Cl.$^6$ ................................................ A61M 31/00
[52] U.S. Cl. ........................ 604/57; 128/754; 606/170
[58] Field of Search .................... 604/93, 95, 117, 604/158, 159, 160, 164, 165, 166, 170, 48, 57, 59, 60; 128/751, 753, 754, 755, 749; 606/7, 167, 170, 184, 185, 187

[56] References Cited

U.S. PATENT DOCUMENTS

| | | |
|---|---|---|
| 3,477,423 | 11/1969 | Griffith . |
| 3,606,878 | 9/1971 | Kellogg . |
| 4,178,810 | 12/1979 | Takahashi . |
| 4,600,014 | 7/1986 | Beraha ................................ 128/754 |
| 4,609,370 | 9/1986 | Morrison ............................. 604/165 |
| 4,699,154 | 10/1987 | Lindgren ............................ 128/754 |
| 4,702,261 | 10/1987 | Cornell et al. ..................... 128/754 |
| 4,776,346 | 10/1988 | Beraha et al. ...................... 128/754 |
| 4,871,094 | 10/1989 | Gall et al. .......................... 222/386 |
| 4,881,551 | 11/1989 | Taylor ................................ 128/754 |
| 4,900,304 | 2/1990 | Fujioka et al. ..................... 604/60 |
| 4,907,598 | 3/1990 | Bauer ................................. 128/753 |
| 4,913,142 | 4/1990 | Kittrell et al. ...................... 606/7 |
| 4,917,100 | 4/1990 | Nottke ................................ 128/749 |
| 4,940,061 | 7/1990 | Terwilliger et al. ................ 128/754 |
| 4,958,625 | 9/1990 | Bates et al. ........................ 128/754 |
| 4,986,814 | 1/1991 | Burney et al. ..................... 604/164 |

FOREIGN PATENT DOCUMENTS

| | | |
|---|---|---|
| 0207726 | 7/1987 | European Pat. Off. . |
| 89/10091 | 11/1989 | WIPO . |
| 91/10399 | 7/1991 | WIPO . |

*Primary Examiner*—C. Fred Rosenbaum
*Assistant Examiner*—V. Alexander
*Attorney, Agent, or Firm*—Hamilton, Brook, Smith & Reynolds

[57] ABSTRACT

A subcutaneous drug delivery device having a driving member for advancing a piston, concentrically enclosed by a cannula, to deliver a drug pellet to a subcutaneous tissue site. The piston has a recessed distal platform upon which the pellet rests for delivery when the distal end of the piston is exposed beyond the cannula.

5 Claims, 2 Drawing Sheets

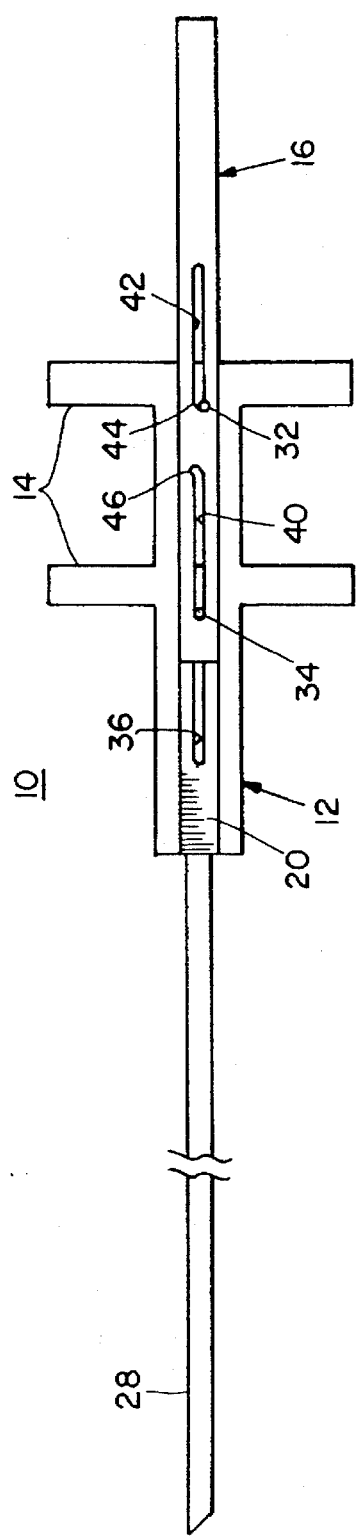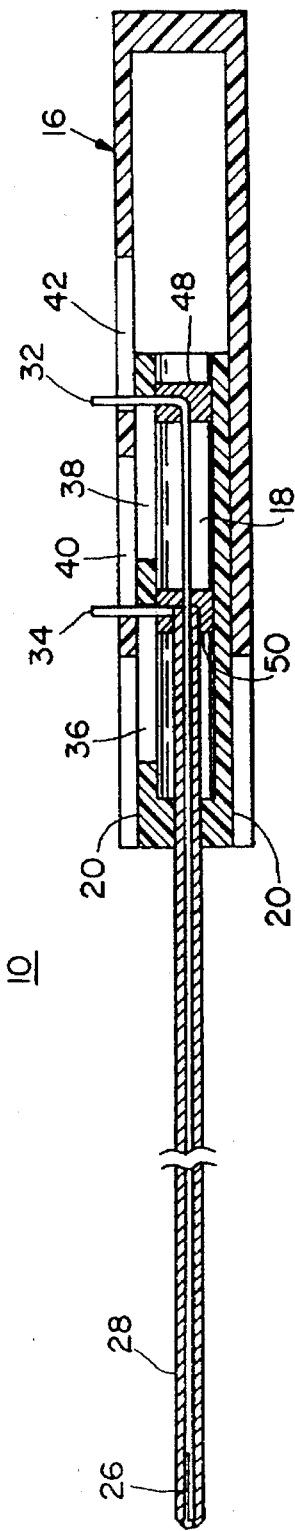

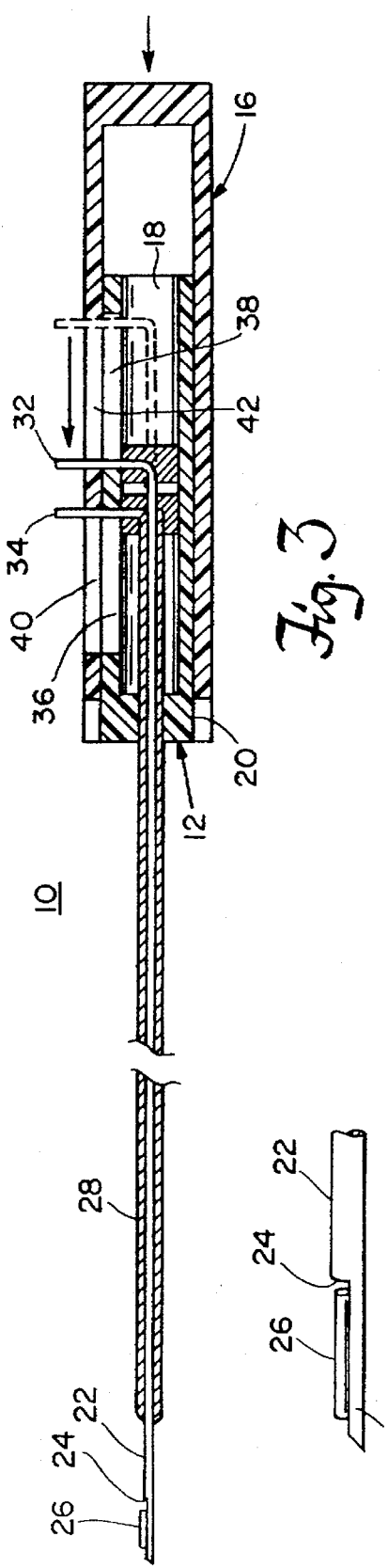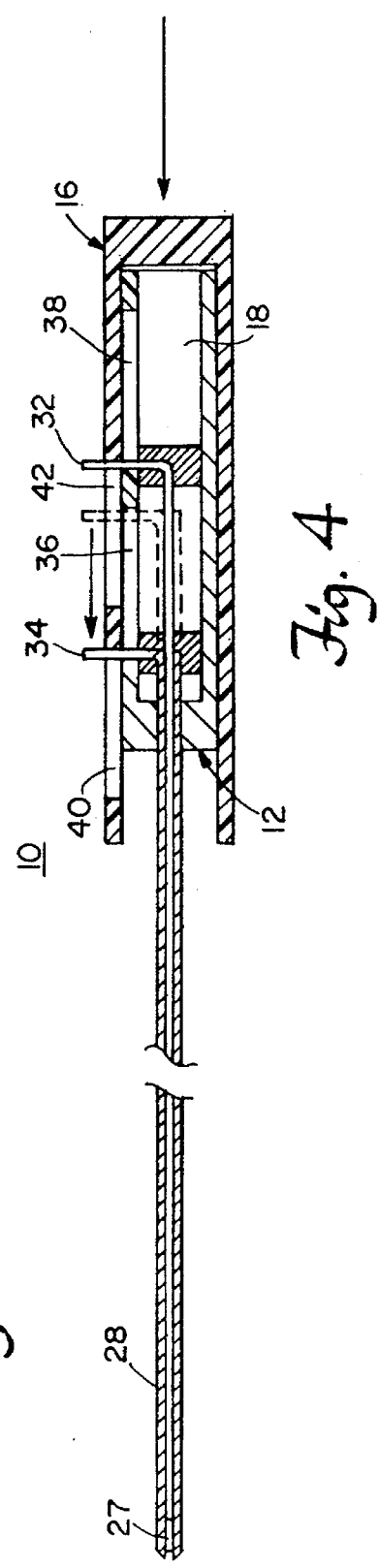

SUBCUTANEOUS DRUG DELIVERY DEVICE

This is a continuation of application Ser. No. 07/965,638 filed Oct. 23, 1992 now U.S. Pat. No. 5,358,474, which is a continuation-in-part of Ser. No. 07/908,353 filed Jul. 6, 1992 now abandoned which is a continuation-in-part of Ser. No. 724,706, filed Jul. 2, 1991 now U.S. Pat. No. 5,127,419 which is issued on Jul. 7, 1992, each of which is incorporated herein by reference.

BACKGROUND OF THE INVENTION

Much effort has been expended in recent years to find an effective and superior way of administering drugs to patients' bodies. Products such as the transdermal patch and once-a-day orally administered pills that more precisely deliver drugs have been developed. Such products are a boon to patients for they boost the effectiveness of the drugs and limit side effects by precisely controlling how quickly drugs are released in the body; by keeping drugs at a constant level and by delivering them exactly where needed.

One such development is the injection or implantation of drugs in the form of in microscopic particles or pellets at a disease site. The drugs are encapsulated in polymers or fatty compounds, such as liposomes which permit slow release of the encapsulated drug over time thereby potentially lowering the drugs toxicity.

SUMMARY OF THE INVENTION

The subject invention relates to an improved instrument for subcutaneous delivery of drug pellets to patients. The instrument is comprised of a driving member which sequentially advances a piston having a piston notch at a distal end for supporting the drug to be delivered and a cannula concentrically enclosing the piston during delivery. Note: For reference purposes, the end of the device nearest the driving member is referred to as the proximal end and the end of the device having the piston notch is referred to as the distal end.

The instrument includes a housing with a bore extending along a longitudinal axis of the housing. A track in the housing extends parallel to the bore. The track has a proximal and distal housing slot extending along the longitudinal axis. A piston and a cannula are mounted in the bore and extend coaxially along the longitudinal axis. The driving member is slideably engaged in the track for longitudinal movement therein and the driving member also contains a proximal and distal elongate slot. A piston coupling means extends to the piston through the proximal elongate slot in the housing and the driving member. Optionally, a cannula coupling means extends to the cannula through the proximal elongate slot in the housing and the driving member.

The drug, preferably in slow-release pellet form is placed on the notch when the instrument is in the fully retracted position and the cannula forms a sheath over the pellet. The physician places the distal end of the instrument adjacent the tissue region where the drug is to be delivered and inserts the instrument subcutaneously to the intended delivery spot. Then the driving member is moved distally along the track toward the piston notch. This extends the piston notch beyond the sheath provided by the cannula whereupon the pellet is exposed and can then be deposited at the desired spot. Optionally, as the driving member is moved further along the track the cannula is extended until the cannula coupling means reaches the distal end of the distal housing slot. In this, the fully advanced position, the cannula again covers the piston notch at the tip of the piston and the instrument may be retracted leaving the pellet deposited in the desired tissue site.

A significant advantage of the invention is that the physician may advance the piston by unidirectional single-handed movement of the driving member in a single, smooth and uninterrupted motion and precisely deposit the drug at the predetermined tissue site.

BRIEF DESCRIPTION OF THE FIGURES

FIG. 1 is a top view of an embodiment the instrument of this invention.

FIG. 2 is a cross-section side view of the instrument of this invention in the fully retracted position.

FIG. 3 is a cross-section side view of the instrument of this invention in a partially advanced position.

FIG. 3a is an enlarged view of an embodiment of the distal or tip end of the piston.

FIG. 4 is a cross-section side view of the instrument in a fully advanced position.

DESCRIPTION OF A PREFERRED EMBODIMENT

Considering now the drawings in detail, FIG. 1 shows a top view of an embodiment of the instrument. The instrument 10 has a housing 12 with a pair of finger grips 14 extending transverse the longitudinal axis of the housing. A driving member 16 is slideably engaged with a track 20 formed along the longitudinal length of housing 12.

Referring to FIG. 2, which is a cross-sectional side view of the FIG. 1 embodiment, the housing track 20 has an elongate proximal housing slot 38 and an optional elongate distal housing slot 36 which extend along the longitudinal axis. The driving member 16 also has an elongate proximal slot 42 and an optional elongate distal slot 40. The proximal and distal driving member slots 42 and 40, respectively, are provided with notches 44 and 46 respectively at their distal and proximal ends, respectively. The notch in the proximal driving member slot 42 is designated notch 44 and the notch in the distal driving member slot 40 is designated notch 46 (shown most clearly in FIG. 1).

The housing has a cylindrical bore 18 formed therein which extends along the longitudinal axis of the housing 12. Mounted within the cylindrical bore 18 and extending along the longitudinal axis is a piston 22 and a cannula 28 mounted coaxial to the piston 22. The piston 22 and cannula 28 are secured at their respective proximal ends by a piston grip 48, and a cannula grip 50. The piston grip 48 and cannula grip 50 are disc-shaped with a diameter which approximates the diameter of the cylindrical bore. The piston grip 48 and the cannula grip 50 are slideably engaged within the housing bore 18. The piston grip 48 and cannula grip 50 have respective channels formed therein through which drive pins 32 and 34 respectively extend for engagement with the proximal ends of the piston and cannula respectively.

The piston and cannula are preferably formed of rigid sterilizable material such as stainless steel. Other components of the device, including the housing, driving member, piston and cannula grips, etc. are preferably manufactured from low cost plastic material. The use of molded plastic components for the manufacture of the instrument is preferred to lower the cost so that the device can be disposed of after use.

To use the instrument of this invention to subcutaneously deposit a drug, the physician begins with the device in the fully retracted position as shown in FIG. 2 so that the distal end of the cannula encloses the piston. In this position, the driving member 16 is withdrawn to its most proximal position and the cannula drive pin 34 is located at the proximal terminus of housing slot 36 and the distal terminus of driving member slot 40. The piston drive pin is located at the proximal terminus of housing slot 38 and engaged in the notch 44 at the distal terminus of driving member slot 42. Preferably, the drug pellet 26 has been disposed upon the platform provided on piston 22 by the piston notch 24 formed at the distal end of the piston as most clearly shown in FIG. 3A.

With the cannula concentrically enclosing the piston tip and drug pellet 26 the end of the device is positioned at a point within the body proximate to the tissue site for drug delivery. The physician then advances the driving member 16 toward the distal end of the device. As the driving member is advanced, the piston drive pin 32 remains locked in notch 44 resulting in the advance of the distal tip 24 of the piston 22 into the tissue. The cannula drive pin 34, on the other hand, remains stationary. As the driving member 16 advances from the original fully retracted position, the proximal terminus of driving member slot 40 advances toward stationary cannula pin 34.

FIG. 3 shows the relationship of the parts at the point at which the piston 22 is fully advanced and the cannula 28 is fully retracted. In this position, the pellet 26 is now exposed and can be deposited into the tissue and the device withdrawn. The cannula drive pin 34 is now in contact with the proximal termini of both driving member slot 40, and housing slot 36. The piston drive pin 32 is in contact with the distal terminus of housing slot 38, and engages notch 44 at the distal terminus of driving member slot 42. The device may then be withdrawn from the body.

Alternatively, after the pellet is deposited the physician can continue to advance the driving member distally, the resistance of the housing on piston drive pin 32 (which has reached the distal terminus of housing slot 38) forces the piston drive pin out of notch 44 and into driving member slot 42. This results in loss of motion of the piston 22 and the proximal terminus of driving member slot 42 advances toward the piston drive pin 32 as the physician continues to advance the driving member 16. At approximately the same time that the piston drive pin 32 is forced from notch 44, the cannula drive pin 34 begins its distal advance. The cannula drive pin 34 is engaged with notch 46 at the proximal terminus of driving member slot 40. As the driving member 16 is advanced, the cannula drive pin 34 and the cannula 28 itself are driven distally. The cannula in this position, as shown in FIG. 4, encloses the platform 27 formed at the notched end of piston 22 and the device may then be withdrawn from the body.

For deeper penetration into the body, the shaft of the piston and cannula may be elongate and made from a semi-rigid material so that bends can be introduced during insertion, for example, to avoid possible contact with vital organs. The mechanism of sequential piston and cannula advancement is identical in the remote embodiment to that described above.

Equivalents

Those skilled in the art will know, or be able to ascertain using no more than routine experimentation, many equivalents to the specific embodiments of the invention described herein. For example, the term "drug" as used herein is intended to have a broad construction so as to include any type of medication capable of being administered subcutaneously in the manner described herein. Also, the tip end of the piston longitudinally ahead of the drug may be provided with a post or barrier (not shown) of diameter slightly less than the diameter of the opening in the cannula 28 so that the drug is not only concentrically enclosed by the cannula until delivery but is also longitudinally enclosed by the barrier at the end of the piston. These and all other equivalents are intended to be encompassed by the following claims.

I claim:

1. A surgical instrument comprising:
   a) a housing with a bore extending along a longitudinal axis of the housing and a track extending parallel to the bore, said track having an elongate proximal housing slot and an elongate distal housing slot extending along the longitudinal axis;
   b) a piston having a distal tip end and a cannula mounted coaxially thereto and within the bore extending along the longitudinal axis thereof;
   c) a driving member slideably engaged in said track for longitudinal movement therein, the driving member having a proximal elongate slot with a notch formed therein and a distal elongate slot with a notch formed therein, said slots extending along the longitudinal axis;
   d) a piston drive pin for engaging the piston with the driving member, the piston drive pin extending from the piston in a direction perpendicular to the longitudinal axis through the proximal housing slot and the proximal driving member slot, the piston drive pin engaging the piston with the driving member by movement of the driving member distally long the track toward the piston tip end, the piston capable of being extended until the piston drive pin reaches the distal end of the proximal housing slot; and
   e) a cannula drive pin for engaging the cannula with the driving member, the cannula drive pin extending from the cannula in a direction perpendicular to the longitudinal axis through the distal housing slot and the distal driving member slot, the piston drive pin engaging the cannula with the driving member when the piston drive pin is at the distal end of the proximal housing slot, the cannula capable of being extended by movement of the driving member further along the track toward the piston tip end until the cannula drive pin reaches the distal end of the distal housing slot.

2. The instrument of claim 1 wherein the proximal terminus of the piston is mounted within a piston grip and the proximal terminus of the cannula is mounted within a cannula grip, the piston grip and the cannula grip being engaged slideably within the housing bore.

3. The instrument of claim 1 wherein the notch in the proximal slot is located at a distal end of the proximal slot for engaging the piston drive pin and the notch in the distal slot is located at a proximal end of the distal slot for engaging the cannula drive pin.

4. The instrument of claim 3 wherein the piston has a tip with a resected portion adjacent the tip.

5. The instrument of claim 4 wherein the housing has finger grips extending therefrom transverse said longitudinal axis.

* * * * *